United States Patent [19]
Mathys et al.

[11] Patent Number: 5,672,800
[45] Date of Patent: Sep. 30, 1997

[54] ALKENE OLIGOMERIZATION

[75] Inventors: Georges Marie Karel Mathys, Bierbeek; Luc Roger Marc Martens, Meise; Marleen Augusta Baes, Oud-Heverlee; Johannes Petrus Verduijn, Leefdaal; Diane Renata Cornelia Huybrechts, Oud-Turnhout, all of Belgium

[73] Assignee: Exxon Chemical Patents Inc., Wilmington, Del.

[21] Appl. No.: 256,950

[22] PCT Filed: Jan. 27, 1993

[86] PCT No.: PCT/EP93/00177

§ 371 Date: Aug. 29, 1994

§ 102(e) Date: Aug. 29, 1994

[87] PCT Pub. No.: WO93/16020

PCT Pub. Date: Aug. 19, 1993

[30] Foreign Application Priority Data

Jan. 30, 1992 [EP] European Pat. Off. .............. 92300797

[51] Int. Cl.⁶ ............................................. C07C 2/02
[52] U.S. Cl. ...................... 585/520; 585/530; 585/531; 585/532; 585/533
[58] Field of Search ............................. 585/530, 531, 585/532, 533, 520

[56] References Cited

U.S. PATENT DOCUMENTS

| | | | |
|---|---|---|---|
| 4,160,788 | 7/1979 | Young | 585/475 |
| 4,481,177 | 11/1984 | Valyocsik | 423/329 |
| 4,788,374 | 11/1988 | Chu et al. | 585/533 |
| 4,831,205 | 5/1989 | Krambeck et al. | 585/533 |
| 4,868,146 | 9/1989 | Chu et al. | 502/71 |
| 5,043,499 | 8/1991 | Haradi et al. | 585/533 |

FOREIGN PATENT DOCUMENTS

| | | | |
|---|---|---|---|
| 276095 | 7/1988 | European Pat. Off. | C07C 2/12 |
| 299671 | 1/1989 | European Pat. Off. | C07C 2/12 |
| 318132 | 5/1989 | European Pat. Off. | C07C 2/00 |
| 323032 | 7/1989 | European Pat. Off. | C07C 2/00 |
| 377306 | 8/1992 | European Pat. Off. | C10G 69/12 |
| WO89/07586 | 8/1989 | WIPO . | |

*Primary Examiner*—Glenn A. Caldarola
*Assistant Examiner*—Elizabeth D. Wood
*Attorney, Agent, or Firm*—John F. Hunt; John J. Mahon; Catherine L. Bell

[57] ABSTRACT

In a process for the oligomerization of $C_2$–$C_{12}$-alkenes, an alkene-containing feedstock having a water content of from 0.05 to 0.25 molar %, based on the hydrocarbon content of the feedstock, is passed over a zeolite catalyst. Improved alkene conversion and catalyst life are obtained compared to processes in which non-hydrated feedstocks are used.

8 Claims, 5 Drawing Sheets

ALKENE OLIGOMERIZATION

This invention relates to the oligomerisation of alkenes and to catalysts used in alkene oligomerisation processes in particular for the production of $C_5$ to $C_{15}$ olefins which may be subsequently subject to hydroformylation for the production of aldehydes and alcohols themselves useful in the production of plasticiser esters, mercaptans and surfactants.

In one form of olefin oligomerisation a solid phosphoric acid catalyst is used as catalyst. A significant amount of cracked products is produced, the phosphoric acid catalyst is not regenerable and its disposal in an environmentally acceptable manner is difficult and expensive.

Zeolite catalysts of many types have been proposed for the conversion of lower molecular weight olefins (that is, olefins having up to twelve carbon atoms) into olefinic hydrocarbons of higher molecular weight. The higher molecular weight olefins may be used in a variety of chemical processes, for example, in the manufacture of fuel oil, synthetic lubricants, alcohols, plasticisers and mercaptans.

International Patent Application WO 89/07586 discloses a process for conversion of a fuel gas containing ethene and propene and a catalytic reformate containing $C_6$ to $C_8$ aromatic hydrocarbons into hydrocarbon products of higher molecular weight. The fuel gas and reformate feedstocks are contacted at elevated temperature and pressure with a zeolite catalyst, which may be of the ZSM-5 type. If ZSM-5 pentasil type crystals are used, the catalyst crystals preferably have a size of from 0.01 to over 2 microns. WO 89/07586 indicates that the zeolites ZSM-22 and ZSM-23 may be used.

U.S. Pat. No. 4,868,146 discloses a catalyst having a crystalline metallosilicate inner core and an inactive porous shell, which may be used, for example, to catalyse the oligomerisation of lower olefins. Highly siliceous zeolites, including, for example, ZSM-22, may be used. U.S. Pat. No. 4,788,374 similarly discloses an olefin oligomerisation catalyst having a crystalline metallosilicate core and a porous shell.

European Specification 377306 discloses a process in which branched internal olefins are co-oligomerised with alpha-olefins to give a synthetic lube-range product. In a first step, propene is converted by contact with a zeolite catalyst of the ZSM-5 type to a mixture of oligomers. In a number of the Examples a ZSM-23 catalyst that has been prepared in accordance with U.S. Pat. No. 4,160,788 is used.

European Specifications 276095, 323032 and 318132 disclose processes for oligomerising light olefins using zeolite catalysts.

U.S. Pat. No. 4,481,177 discloses the use of ZSM-22 in the organic nitrogen-containing and alkali-metal containing form. That form is apparently obtained by cation exchange of the ZSM-22 with an alkyl- or aryl-ammonium ion. U.S. Pat. No. 4,481,177 also suggests that ZSM-22 may be used to catalyse various chemical reactions, including olefin oligomerisation. There is no Example, however, of any olefin oligomerisation.

European Specification 0299671 discloses the production of high viscosity index lubricating oils by the oligomerisation of lower olefins over ZSM-5 zeolite catalysts by cofeeding small amounts of water with the hydrocarbon stream. The lubricating oils have a boiling point above 343° C. and it is speculated that the presence of the water enhances the intracrystalline acid site polymerisation in preference to surface active site polymerisation leading to the formation of more linear lubricant range hydrocarbons and thus an enhancement in viscosity index.

It has now been found that, unexpectedly, by using in an alkene oligomerisation process an alkene-containing feedstock with a water content of from 0.05 to 0.25 molar %, and preferably of at least 0.06 molar %, based on the hydrocarbon content of the feedstock, the yields of the desired higher molecular weight alkenes can be increased, and the catalyst becomes deactivated more slowly.

The invention provides a process for improving the yield and prolonging catalyst life in oligomerising at least one alkene having from 2 to 12 carbon atoms, (hereinafter referred to for simplicity as "$C_2$–$C_{12}$-alkenes") comprising contacting a $C_{2-C12}$-alkene-containing feedstock having a water content of 0.05 to 0.25 molar %, based on the hydrocarbon content of the feedstock, with a zeolite catalyst.

The invention is particularly concerned with the production of $C_5$ to $C_{20}$ olefins of initial boiling point 30° to 310° C., preferably 30° to 300° C., more preferably 30° to 250° C., from propylene and/or butene feedstocks. In particular the production of the following olefins.

| Products | Distillation Range, °C. ASTM D1078 | |
|---|---|---|
| | Initial Boiling Point | Dry Point |
| Pentenes | 30 | |
| Hexanes | 63 | |
| Heptenes | 88 | 97 |
| Octenes | 114 | 126 |
| Nonenes | 135 | 143 |
| Decenes | 155 | 160 |
| Undecenes | 167 | 178 |
| Dodecenes | 185 | 194 |
| Tetramer K | 181 | 200 |
| Tetramer V | 186 | 198 |
| Tetramer D | 186 | 224 |
| Tetramer P | 189 | 225 |
| Tridecenes | 204 | 213 |

In addition to enabling the yields of higher molecular weight alkenes to be increased, the process of the invention enables the oligomerisation reaction to be carried out at relatively low temperatures. Preferably, the contacting of the feedstock with the catalyst is carried out at a temperature not exceeding 260° C. Advantageously, the said contacting is carried out at a temperature of from 180° to 255° C.

In the case of an alkene-containing feedstock having a water content of less than 0.05 molar %, the water content may be increased by any suitable means. For example, the feedstock can be passed through a thermostatted water saturator. Since the amount of water required to saturate the alkene feedstock will depend upon the temperature of the feedstock, control of the water content can then be effected by appropriate control of the temperature of the feedstock. The water content of the feedstock is preferably at least 0.06 molar %, based on the hydrocarbon content of the feedstock.

The zeolite catalyst may be any catalyst that is active in alkene oligomerisation reactions. For example, there may be used a catalyst selected from the group consisting of zeolites of the TON structure type (for example, H-ZSM-22, H-ISI-1, H-Theta-1, H-Nu-10, KZ-2), or zeolites of the MTT structure type (for example, H-ZSM-23, KZ-1) or zeolites of the MFI structure type (for example, H-ZSM-5) or zeolites of the MEL structure type (for example, H-ZSM-11) or zeolites of the MTW structure type (for example, H-ZSM-12), or zeolites with the EUO structure type (for example, EU-1), or zeolite H-ZSM-57, or any member of the ferrierite structure family. Other examples of suitable catalysts are offretites, H-ZSM-4, H-ZSM-18 or zeolite Beta. Reference is made to "Synthesis of High-Silica Aluminosilicate Zeolites" by P. A. Jacobs and J. A. Martens (published as volume 33 in the series "Studies in Surface Science and Catalysis") for a review of the synthesis and properties of the aforementioned zeolites.

Additionally, the catalyst can be a zeolite synthesized without addition of a template, for example, faujasites, zeolite L, mordenites, erionites and chabazites, the structures of which are contained in the "Atlas of Zeolite Structure Types" by W. M. Meier and D. H. Olson (published by Butterworths on behalf of the Structure Commission of the International Zeolite Association). Zeolite catalysts having crystal structures that are essentially the same as the crystal structures of the above-mentioned zeolite catalysts but differ slightly therefrom in chemical composition may also be used, for example, zeolite catalysts obtained by removal of a number of aluminium ions from, or by steaming of, the above-mentioned zeolite catalysts, or zeolite catalysts obtained by addition of different elements, for example, by impregnation or cation exchange or by incorporation during the zeolite synthesis (for example boron, iron and gallium).

The zeolite catalyst may advantageously be a modified zeolite catalyst, as hereinafter defined, that has crystals of needle morphology, the ratio of the length to the diameter (L/D) of the crystals being not less than 3.

Preferably, H-ZSM-22, or a modified zeolite catalyst, as hereinafter defined, having the crystalline structure of ZSM-22 is used as the catalyst. Advantageously, there may be used crystals of H-ZSM-22 or of a modified zeolite catalyst, as hereinafter defined, having the crystalline structure of ZSM-22, the length of at least 75% of which do not exceed 10 μm and, more preferably not larger than 1.3μ.

The process of the invention may be used with particular advantage in the oligomerisation of $C_3$–$C_6$-alkenes.

The water content of the alkene-containing feedstock is preferably from 0.08 to 0.25 molar %, more especially 0.1 to 0.2 molar %, based on the hydrocarbon content of the feedstock. If, as may be desired, the alkene-containing feedstock contains as diluent a hydrocarbon gas other than a $C_2$–$C_{12}$-alkene, for example, a saturated hydrocarbon gas, that other hydrocarbon is to be included in the hydrocarbon content for the purposes of calculation of the water content.

Zeolite catalysts (other than modified zeolite catalysts, as hereinafter defined) may be made by any suitable method, for example, by heating a reaction mixture containing a source of silicon oxide, a source of aluminium oxide and, if appropriate, an organic promoter, for example, a nitrogen or phosphorus-containing organic base, together optionally with an alkali metal base, and separating the porous aluminosilicate crystals (zeolite precursor crystals) formed. The precursor crystals are then generally calcined in air or oxygen at a temperature exceeding 500° C., for example, at a temperature of 550° C. for, for example, 10 to 20 hours. It is thought that, during calcination at such temperatures, the residual organic promoter remaining in the pores of the crystals is burnt substantially completely so that the pores are voided. The calcined material is preferably exchanged with ammonium ions ($NH_4^+$) and subjected to conditions under which the ammonium ions decompose, with the formation of ammonia and a proton, thus producing the acidic form of the zeolite. Alternatively the acid form may be obtained by acid exchange with, for example, hydrochloric acid. If desired, however, the calcined material may be used as a catalyst without first being exchanged with ammonium ions, since the material then already possesses acidic sites. The activity of the material is then significantly lower than that of a material that has been exchanged with ammonium ions and then subjected to conditions under which the ammonium ions decompose.

The term "modified zeolite catalyst" is used throughout the specification, including the claims, to mean a zeolitic material that has been formed by a method in which an organic substance (organic promoter or template) is used to promote formation of aluminosilicate crystals (zeolite precursor crystals) having the desired zeolitic structure, the uncalcined zeolite precursor crystals are exchanged with ammonium ions or protons, and the crystals are then calcined in conditions that are such that a portion of the organic promoter or of a decomposition product derived therefrom remains within the pores of the crystal.

Surprisingly, if needle-shaped aluminosilicate crystals (that is aluminosilicate crystals having needle morphology with a length to diameter (L/D) ratio of not less than 3) are exchanged with ammonium ions without first being subjected to the calcination step at a temperature exceeding 500° C. customarily employed in the previously known methods, and then calcined under conditions such that the promoter remains, or decomposition products thereof remain, in the pores, the modified zeolite catalyst so obtained has a greater catalytic activity, giving good conversion with relatively little formation of cracked or saturated products or aromatics, and becomes deactivated in use more slowly, than material that has been calcined at temperatures exceeding 500° C. prior to exchange with ammonium ions.

The present invention further provides a process for oligomerising $C_2$–$C_{12}$-alkenes comprising contacting a $C_2$–$C_{12}$-alkene-containing feedstock with a modified zeolite catalyst, as hereinbefore defined, having needle morphology with a L/D ratio of not less than 3 and a length not exceeding 30 μm. The modified zeolite catalyst is preferably one having the crystalline structure of ZSM-22.

The modified zeolite catalyst used in the processes described in the present specification may, for example, be prepared by (i) heating a reaction mixture comprising
  (a) a source of silicon oxide ($SiO_2$)
  (b) a source of aluminium oxide ($Al_2O_3$)
  (c) optionally, an alkali metal source
  (d) a nitrogen- or phosphorus-containing organic base, and
  (e) water;
(ii) separating the formed crystals from the reaction mixture;
(iii) exchanging with ammonium ions or protons; and
(iv) calcining the crystals under conditions such that a portion of the organic base or of decomposition products thereof remains within the crystal pores.

The organic base used in step (i) above may be, for example, a base containing a radical $R_4N^+$ in which the R groups may be the same or different and each may be hydrogen, an alkyl group containing from two to eight carbon atoms or an aryl group containing up to eight carbon atoms. Preferably, however, the base is an amine, for example, an alkyl amine having from two to eight carbon atoms or an aryl amine having up to eight carbon atoms. More than one amine group may be present. For example, for the manufacture of ZSM-22, the base may especially advantageously be 1,6-diaminohexane.

The exchange with ammonium ions in step (iii) may be carried out by any suitable method, for example, by treating the crystals with an aqueous solution of ammonium chloride, ammonium nitrate or ammonium hydroxide. Hydrochloric acid treatment may be achieved by contacting the crystals with a dilute acid solution.

In step (iv), the crystals may be calcined at a temperature of from 120° to 430° C. for from 5 hours to several days, generally at temperatures above 150° C. The temperatures in the upper part of the specified temperature range correspond to the shorter heating times and the temperatures in the lower part of the specified temperature range correspond to the longer heating times.

Thus, for example, crystals may be calcined at a temperature of 400° C. for from 5 to 20 hours. At a temperature of 120° C., longer calcination times of at least 2 days and preferably from 3 to 5 days will generally be necessary to achieve adequate voiding of the pores.

The calcination conditions should be chosen such that whereas sufficient of the organic base (template) is burnt that the pores are to a significant extent voided they still contain some base or decomposition products thereof. The presence of the said base or decomposition products is indicated by a substantial discolouration of the crystals, as compared with the bright white material that is normally obtained after calcination at temperatures exceeding 500° C. Thus, for a given temperature, the calcination time should be so selected that, while the crystals have a colour that is distinctly non-white, indicating the presence of decomposition products of the organic base, the pores are to a substantial extent voided. The extent to which the pores have been voided may be ascertained, for example, by measuring the net adsorption capacity of the crystals using n-hexane. This may be done by contacting the crystals with nitrogen gas saturated with n-hexane at 30° C., and then monitoring the amount of n-hexane desorbed in a nitrogen atmosphere at the same temperature.

By way of example, the net adsorption capacity of the modified ZSM-22 used in accordance with the invention should preferably be reduced by not more than 50%, more preferably, by not more than 25%, as compared with the net adsorption capacity of ZSM-22 that has been obtained by a process in which calcination has been carried out at 550° C. for 16 hours both before and after exchange with ammonium ions. For other zeolite catalysts, the preferred maximum reduction in the net adsorption capacity of the modified zeolite catalyst as compared with the corresponding unmodified catalyst may differ from that for ZSM-22, but the determination of preferred reductions for those other catalysts will be a matter for routine experiment.

The crystals may in some cases contain a minor proportion of crystalline material of a second aluminosilicate having a crystal structure that differs from the crystal structure of the aluminosilicate that forms the major proportion of the crystals, the proportion of the second aluminosilicate generally being sufficiently small that the properties of the crystal as a whole, including the external characteristics of the crystal, are determined predominantly by the aluminosilicate that constitutes the major proportion of the crystal. For example, a modified zeolite catalyst consisting of a major proportion of aluminosilicate material having the crystalline structure of ZSM-22, with co-crystallised aluminosilicate impurities having the crystalline structure of ZSM-5 and crystoballite, may be used.

The preferred molar ratios of the different reactants/ silicon oxide source in the manufacture of H-ZSM-22 and the modified zeolite catalyst having the crystalline structure of ZSM-22 used in accordance with the present invention are as follows:

|  | Molar Ratio (MR) | MR (preferred) |
|---|---|---|
| $SiO_2/Al_2O_3$ | 30–190 | 90 |
| $H_2O/SiO_2$ | 10–60 | 40 |
| Template/$SiO_2$ | 0.01–2.0 | 0.3 |
| $M^+/SiO_2$ | 0–2.0 | 0.13–0.25 | where $M^+$ represents an alkali metal ion. The most preferred $M^+/SiO_2$ ratio is 0.25.

Zeolite H-ZSM-22 used in accordance with the present invention preferably has a Si/Al molar ratio of from 20 to 75 and especially of approximately 35.

The zeolite catalysts or modified zeolite catalysts may be used in the form of powders (including powders consisting wholly or in part of single crystals). The zeolite catalysts may instead be incorporated in shaped agglomerates, for example, tablets, extrudates or spheres, which may be obtained by combining the zeolite with a binder material that is substantially inert under the conditions employed in the oligomerisation process. The zeolite catalyst may be present in amounts of from 1 to 99% by weight, based on the combined weight of the zeolite and binder material. As binder material there may be used any suitable material, for example, silica, metal oxides, or clays, such as montmorillonite, bentonite and kaolin clays, the clays optionally being calcined or modified chemically prior to use. Further examples of suitable matrix materials include silica-alumina, silica-berylia, silica-magnesia, silica-thoria, silica-titania, silica-alumina-magnesia, silica-alumina-thoria, silica-alumina-zirconia and silica-magnesia-zirconia.

In a further aspect of the invention there is provided a process for oligomerising $C_2$–$C_{12}$-alkenes comprising contacting a $C_2$–$C_{12}$-alkene-containing feed-stock with crystals of H-ZSM-22 or with crystals of a modified zeolite catalyst having the crystalline structure of ZSM-22, the crystals having a length to diameter ratio of not less than 3 and a length of not greater than 30 µm, preferably not greater than 10 µm and, more especially, not greater than 1 µm.

In an especially preferred process according to the invention, a $C_2$–$C_{12}$-alkene-containing feedstock, more especially a feedstock containing $C_3$–$C_6$-alkenes, having a water content of from 0.05 to 0.25 molar % is contacted with H-ZSM-22 or a modified zeolite catalyst having essentially the crystalline structure of ZSM-22. Especially good yields of dimeric, trimeric and tetrameric products are then obtained. Further, good catalyst activity is observed at relatively low temperatures, for example, at temperatures of from 150°, typically 180°, to 255° C. The proportions of alkanes and aromatics formed are low. The catalyst stability in the process is good in that the catalyst becomes deactivated relatively slowly, as compared with oligomerisation processes where the feedstock is relatively dry.

The zeolite catalysts used in accordance with the invention are regenerable. They are thermally and hydrothermally stable and, for example, can be regenerated by heating in air or oxygen at from 300° to 600° C. or in steam at, for example, 500° C. The average number of branches per molecule of oligomer using H-ZSM-22 or a modified zeolite catalyst having the crystalline structure of ZSM-22 is relatively low compared with that obtained in previously known processes using solid phosphoric acid catalysts. For example nonenes produced from propylene using phosphoric acid catalysts have typically, about 2 branches, whereas those produced using zeolite catalysts have from 1.7 to 1.8 branches. Octenes produced using the phosphoric acid catalyst typically have 1.9 to 2 branches whereas with zeolite catalysis the branching can be lowered to 1.4. The lower branching leading to more reactive products.

The alkenes that may be oligomerised by the processes of the invention are ethene, propene, and linear or branched $C_4$–$C_{12}$-alkenes, which may be mono-, di- or polyunsaturated. As indicated above, however, the alkenes are preferably $C_3$–$C_6$-alkenes. The process is particularly advantageous for the oligomerisation of propene and butenes and may be used for the oligomerisation of a single alkene, or of mixtures of alkenes of the same or of different carbon numbers. The alkene may if desired be diluted with another suitable gas, for example, a low molecular weight saturated hydrocarbon.

The reaction is preferably carried out at pressures higher than atmospheric pressure, for example, at pressures up to 100 bar ($10^7$ Pa).

BRIEF DESCRIPTION OF THE DRAWINGS

Certain illustrative embodiments of the invention will now be described with reference to the accompanying drawings, of which.

In the following Examples, except where indicated to the contrary, $NH_4Cl$ exchanged catalyst crystals had, prior to use, been calcined at a temperature of 550° C. for from 15 to 20 hours in air both before and after exchange, oligomerisation was carried out without hydration of the feedstock, and percentages are by weight except where indicated otherwise.

EXAMPLE 1

Effect of Hydration of Feedstock on Catalytic Activity of H-ZSM-5, H-ZSM-12 and H-ZSM-22

(a)

ZSM-22 precursor crystals having an average length of 1 μm were made by the method described in Example 4(a) below and the crystals were calcined in oxygen for 16 hours at 550° C., exchanged with $NH_4Cl$, and calcined again at 550° C. for 16 hours in oxygen. A feedstock containing, on a hydrocarbon basis, 49.12% propene, 47.95% propane, the balance being ethane and butane was passed over H-ZSM-22 crystals. The product was analysed by gas chromatography (GC) at intervals. After 7 days, feedstock to be fed to the reactor containing the catalyst was hydrated by passing the feedstock, at a temperature of 39° C., through a thermostatted water saturator prior to its introduction into the reactor. The water content of the feedstock prior to its introduction into the water saturator was 0.02 molar % and, on leaving the saturator, the water content was 0.15 molar %, in each case, based on the hydrocarbon content of the feedstock. The pressure in the reactor was maintained at 70 bar ($7\times10^6$ Pa) throughout. The results are summarised in Table 1A.

(b)

A feedstock containing, based on hydrocarbon content, 49.42% propene, 50.50% propane, the balance being ethane and butane, and having an initial water content of 0.02 molar % based on the hydrocarbon content, was hydrated in the manner described in Example 1(a), to give a water content of 0.15 molar % and fed to a reactor containing H-ZSM-12 crystals. The pressure was maintained at 70 bar ($7\times10^6$ Pa). The product was analysed. After 6½ days the feed hydration apparatus was by-passed, feedstock being fed to the reactor without hydration, the unhydrated feedstock having a molar water content of 0.02%, based on the hydrocarbon content. Further reaction conditions and the results are summarised in Table 1B below.

(c)

A feedstock containing approximately 50% propene and 50% propane was hydrated in the manner described in Example 1(a) to give a water content of 0.15 molar % based on the hydrocarbon content and fed to a reactor containing H-ZSM-5 crystals. The reactor was maintained at a pressure of 70 bar ($7\times10^6$ Pa) and, initially, at a temperature of 230° C. The temperature was subsequently raised to 250° C. The product was analysed at intervals. The experiment was then repeated using a feedstock having a water content of 0.02 molar % based on the hydrocarbon content of the feedstock. The results are shown in FIG. 1.

Figure 1:
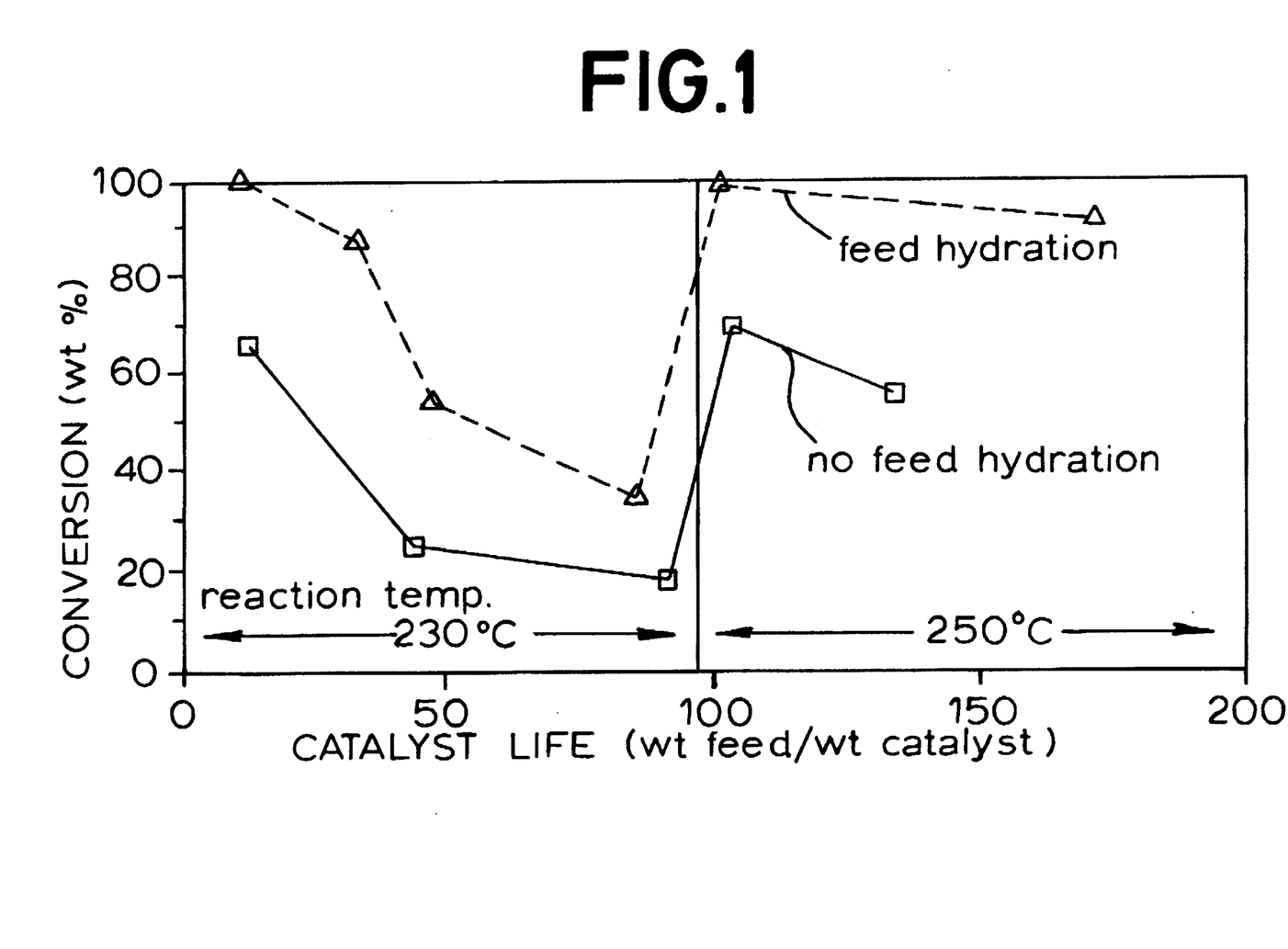
FIG. 1 is a graph showing % conversion of propene against catalyst life for H-ZSM-5.

As is clear from Tables 1A and 1B and from FIG. 1 hydration of the feedstock provides significant advantages. FIG. 1 indicates that, for H-ZSM-5, the % conversion is increased significantly both at 230° C. and 250° C. Table 1A shows that deactivation of H-ZSM-22 occurs relatively quickly when the feed is not hydrated. On commencement of hydration a significant improvement is observed, and an improved level of activity is maintained throughout the experiment subsequently. Thus, deactivation occurs less readily in cases where the feed has been hydrated than where no hydration is carried out. Further, the deactivation that has occurred during the use of unhydrated feed is even reversed by increasing the water content of the feed. A loss of activity is observed upon ceasing hydration of the feedstock in Example 1(b)—see Table 1B.

As will be seen from Tables 1A and 1B, the proportion of saturated reaction product is in each case not more than about 5%. In each case, the amount of aromatics formed was less than 50 ppm.

TABLE 1A

| Hydration (°C.) | NO HYD | NO HYD | NO HYD | NO HYD | NO HYD | 39 | 39 | 39 | 39 | 39 |
|---|---|---|---|---|---|---|---|---|---|---|
| Temperature (°C.) | 205 | 205 | 230 | 230 | 230 | 230 | 230 | 230 | 230 | 230 |
| Space Vel. (weight/Weight · hr) | 1.26 | 1.62 | 1.44 | 1.40 | 1.60 | 1.59 | 1.28 | 1.50 | 1.19 | 1.35 |
| Days on Stream Catlife | 0.83 | 1.83 | 2.83 | 3.83 | 6.83 | 7.83 | 8.83 | 9.83 | 10.83 | 11.88 |
| (weight product/ weight cat) | 9.5 | 13.1 | 29.2 | 42.3 | 72.4 | 87.2 | 100.5 | 116.2 | 128.1 | 142.9 |
| Propene Conversion % | 76.78 | 18.69 | 94.91 | 79.97 | 53.11 | 78.99 | 88.08 | 88.87 | 84.41 | 89.83 |

TABLE 1A-continued

| Selectivity | | | | | | | | | | |
|---|---|---|---|---|---|---|---|---|---|---|
| $C_5$ | 0.56 | 0.29 | 0.64 | 0.48 | 0.38 | 0.51 | 0.51 | 0.52 | 0.30 | 0.59 |
| $C_6$ | 28.34 | 56.18 | 22.87 | 41.78 | 57.17 | 43.30 | 40.62 | 42.13 | 46.02 | 38.40 |
| $C_7$ | 1.35 | 1.06 | 2.32 | 1.50 | 0.98 | 1.32 | 1.31 | 1.34 | 1.41 | 1.56 |
| $C_8$ | 1.67 | 0.49 | 1.74 | 1.05 | 0.68 | 1.02 | 0.94 | 0.99 | 0.99 | 1.20 |
| $C_9$ | 35.06 | 26.78 | 32.33 | 31.37 | 28.05 | 31.79 | 32.02 | 31.34 | 31.69 | 31.85 |
| $C_{10}$ | 2.11 | 1.06 | 2.64 | 1.55 | 0.86 | 1.43 | 1.47 | 1.47 | 1.55 | 1.78 |
| $C_{11}$ | 1.91 | 0.67 | 2.39 | 1.27 | 0.60 | 1.18 | 1.20 | 1.15 | 1.30 | 1.49 |
| $C_{12}$ | 14.83 | 7.77 | 16.39 | 11.53 | 7.35 | 12.20 | 12.59 | 12.23 | 10.87 | 14.14 |
| $C_{13}$ | 2.76 | 0.00 | 3.62 | 1.94 | 0.00 | 0.97 | 1.60 | 1.39 | 0.00 | 2.16 |
| $C_{14}$ | 1.46 | 0.00 | 2.11 | 0.00 | 0.00 | 0.00 | 0.00 | 0.00 | 0.00 | 0.49 |
| $C_{15}$ | 9.94 | 5.70 | 12.94 | 7.51 | 3.92 | 6.28 | 7.74 | 7.43 | 5.87 | 6.35 |
| $C_5$–$C_{15}$ Product from Cracking (%) (*) | 11.82 | 3.57 | 15.47 | 7.81 | 3.51 | 6.43 | 7.04 | 6.86 | 5.54 | 9.27 |
| Saturates in $C_5$–$C_{15}$ Product (%) | 5.1 | 3.1 | 4.8 | 3.2 | 2.4 | 2.8 | 3.5 | 3.0 | | |

(*) SUM of $C_5$ + $C_7$ + $C_8$ + $C_{10}$ + $C_{11}$ + $C_{13}$ + $C_{14}$

TABLE 1B

| | | | | | | | | | |
|---|---|---|---|---|---|---|---|---|---|
| Hydration (°C.) | 40 | 40 | 40 | 40 | 40 | 44 | NO HYD | NO HYD | NO HYD |
| Temperature (°C.) | 180 | 180 | 150 | 170 | 170 | 180 | 180 | 180 | 180 |
| Space Vel. (weight/Weight · hr) | 1.90 | 1.83 | 1.99 | 1.56 | 1.81 | 1.97 | 2.14 | 1.95 | 1.97 |
| Days on Stream | 0.42 | 1.42 | 2.42 | 2.67 | 5.42 | 6.42 | 7.42 | 8.42 | 9.42 |
| Catlife (weight product/weight cat) | 9.3 | 30.3 | 44.5 | 48.6 | 96.7 | 117.4 | 139.1 | 153.7 | 162.1 |
| Propene Conversion (%) | 98.33 | 97.09 | 60.08 | 87.09 | 81.38 | 88.79 | 85.04 | 62.84 | 35.63 |
| Selectivity | | | | | | | | | |
| $C_5$ | 0.70 | 0.49 | 0.22 | 0.46 | 0.40 | 0.47 | 0.47 | 0.47 | 0.66 |
| $C_6$ | 2.61 | 2.38 | 4.75 | 2.88 | 3.27 | 3.17 | 3.98 | 8.30 | 17.35 |
| $C_7$ | 2.85 | 2.57 | 1.15 | 2.05 | 1.91 | 2.47 | 2.52 | 2.54 | 2.51 |
| $C_8$ | 4.60 | 4.36 | 2.24 | 3.87 | 3.66 | 4.40 | 4.34 | 3.84 | 3.07 |
| $C_9$ | 20.67 | 22.50 | 54.25 | 35.28 | 39.56 | 30.90 | 33.86 | 43.10 | 46.13 |
| $C_{10}$ | 5.00 | 4.74 | 2.69 | 4.22 | 3.95 | 4.49 | 4.35 | 3.50 | 2.84 |
| $C_{11}$ | 5.94 | 5.46 | 1.94 | 4.19 | 3.54 | 4.50 | 4.20 | 3.01 | 2.20 |
| $C_{12}$ | 26.39 | 26.88 | 20.80 | 26.18 | 24.72 | 25.91 | 24.80 | 20.20 | 14.96 |
| $C_{13}$ | 6.77 | 6.25 | 2.10 | 4.37 | 3.74 | 4.84 | 4.58 | 3.14 | 2.17 |
| $C_{14}$ | 6.00 | 5.66 | 1.62 | 3.55 | 3.04 | 4.13 | 3.86 | 2.50 | 1.64 |
| $C_{15}$ | 18.47 | 18.72 | 8.24 | 12.95 | 12.22 | 14.71 | 13.04 | 9.38 | 6.46 |
| $C_5$–$C_{15}$ Product from Cracking (%) (*) | 31.86 | 29.52 | 11.96 | 22.70 | 20.23 | 25.30 | 24.33 | 19.01 | 15.09 |
| Saturates in $C_5$–$C_{15}$ Product (%) | 4.7 | | 2.2 | 3.8 | 2.9 | 3.5 | | 3.3 | |

(*) SUM of $C_5$ + $C_7$ + $C_8$ + $C_{10}$ + $C_{11}$ + $C_{13}$ + $C_{14}$

EXAMPLE 2

Effects of Hydration and Temperature on Activity of ZSM-22 and a Modified Zeolite Catalyst having ZSM-22 Crystalline Structure (a)

Figure 2A:
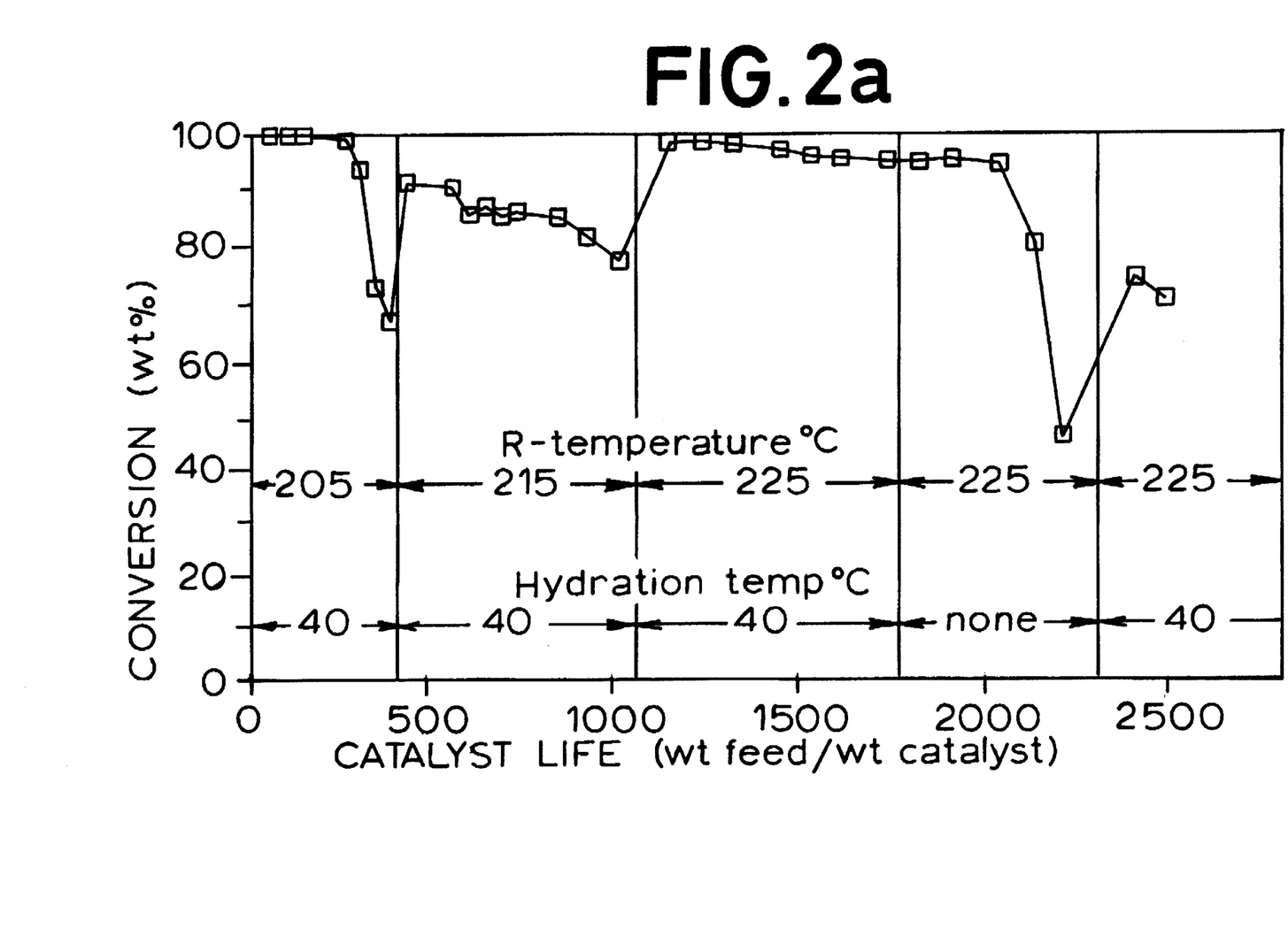
FIG. 2a is a graph showing % conversion of propene against catalyst life for H-ZSM-22.

Precursor crystals of ZSM-22 having an average size of 1 μm were prepared as described in Example 4(a) below and calcined at 550° C. in oxygen for 16 hours, exchanged with aqueous NH$_4$Cl and calcined again at 550° C. for 16 hours to obtain H-ZSM-22. 8.5 g of the H-ZSM-22 crystals so obtained were placed in a reactor. A feedstock consisting of, based on hydrocarbons, 50.68% propene, 48.52% propane, the balance being ethane and butanes, was hydrated by the method described in Example 1(a) to a moisture content of 0.15 molar %, based on the hydrocarbon content. The hydrated feedstock was passed over the catalyst at a temperature of 205° C. and pressure of 70 bar (7×10$^6$ Pa). The space velocity was 1.50 to 2.10 weight/weight.hour. After the conversion had decreased to below 70%, the temperature was increased to 215° C., upon which the conversion increased to approximately 90%. On decrease of the conversion to below 80%, the temperature was increased to 225° C., the conversion then increasing to over 95%. At 225° C. only a relatively slow decrease in conversion was observed. The effect of hydration was then investigated by ceasing hydration, the unhydrated feedstock having a water content of 0.02 molar % based on the hydrocarbon content. A rapid decrease in the conversion was observed. On recommencement of hydration the conversion immediately increased again. Analysis of the hexene isomer distribution showed the hexene product to contain, over the period of the reaction, from 11 to 13% linear hexenes, from 75 to 87% mono-branched hexenes and from 1 to 13% di-branched hexenes. Analysis of the nonene isomer distribution showed the nonene product to contain 1 to 4% linear nonenes, 14 to 40% mono-branched nonenes, 48 to 66% di-branched nonenes and 5 to 19% tri-branched nonenes. FIG. 2a shows the % conversion at a given catalyst life.

(b)

Figure 2B:
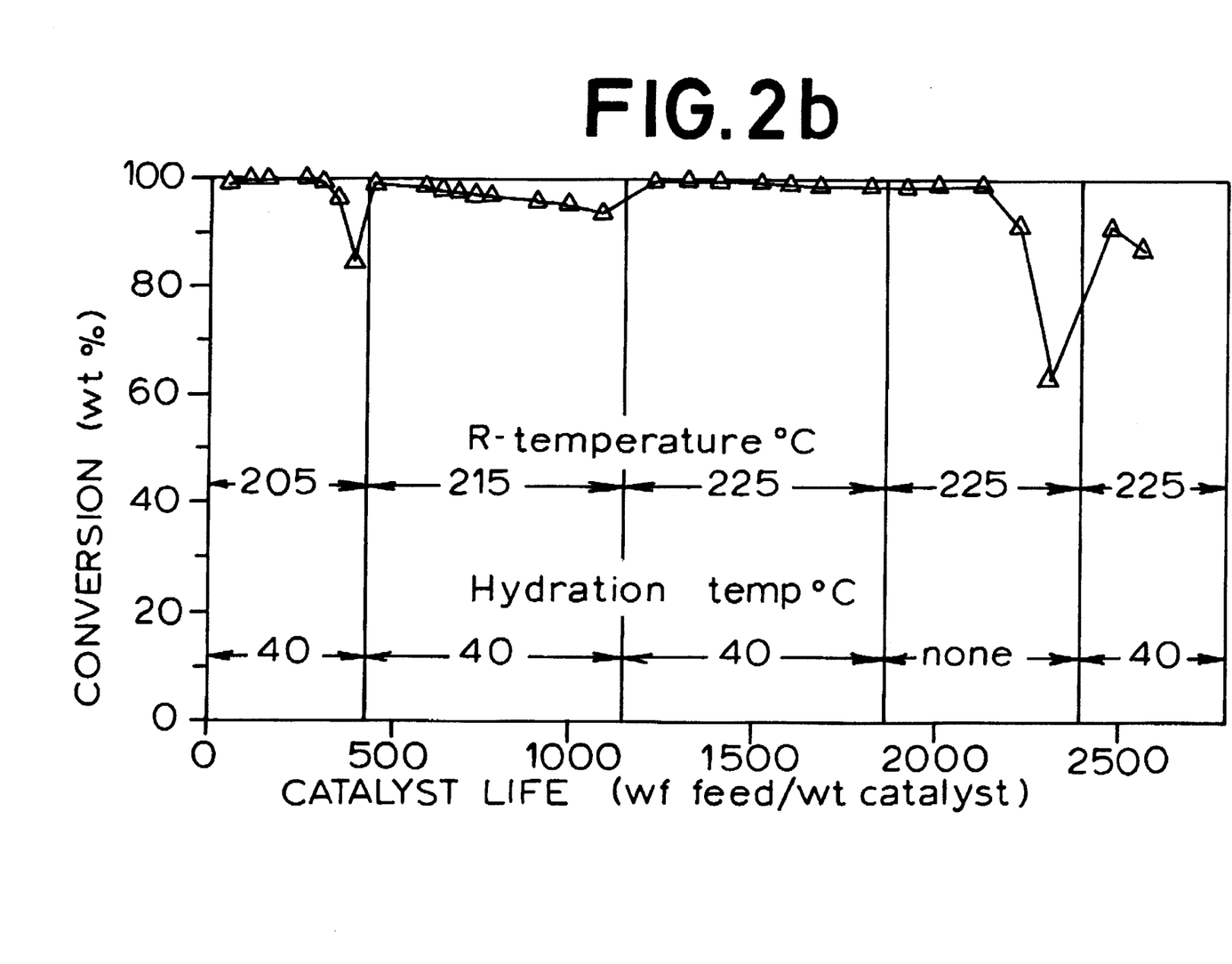
FIG. 2b is a graph showing % conversion of propene against catalyst life for a modified zeolite catalyst having the crystalline structure of ZSM-22.

Precursor crystals of ZSM-22 having an average size of 1 μm were prepared as described in Example 4(a) below, exchanged with NH$_4$Cl and calcined in air at 400° C. for 16 hours to obtain a modified zeolite catalyst having the crystalline structure of ZSM-22. 9.1 g of the calcined crystals were placed in a reactor. A feedstock containing, on a hydrocarbon basis, 50.70% propene, 48.32% propane, the balance being ethane and butanes, was hydrated by the method described in Example 1(a) to a moisture content of 0.15 molar % based on the hydrocarbon content. The hydrated feedstock was passed over the catalyst at a temperature of 205° C. and with a pressure of 70 bar (7×10$^6$ Pa). The space velocity was from 1.60 to 2.20 weight/weight.hour. On observing a decrease in conversion towards 80%, the temperature was increased to 215° C., upon which the conversion increased to almost 100%. A relatively slow decrease in conversion was then observed and the conversion was once again increased to almost 100% by increasing the temperature to 225° C. The effect of hydration was examined by ceasing hydration, the feedstock being fed to the reactor having a water content of 0.02 molar % based on the hydrocarbon content. A rapid decrease in the conversion was then observed. Upon recommencement of hydration, however, the conversion was observed to increase dramatically. The results are shown in FIG. 2b. Analysis of the hexene isomer distribution in the product showed that the hexene fraction contained from 10 to 13% linear hexenes, 72 to 87% mono-branched hexenes and from 1 to 15% di-branched hexenes. The nonene fraction was found to contain from 2 to 4% linear nonenes, from 23 to 40% mono-branched nonenes, from 50 to 62% di-branched nonenes and from 4 to 14% tri-branched nonenes.

EXAMPLE 3

Oligomerisation of Butene Using a Modified Zeolite Catalyst Having the Crystalline Structure of ZSM-22

Figure 3:
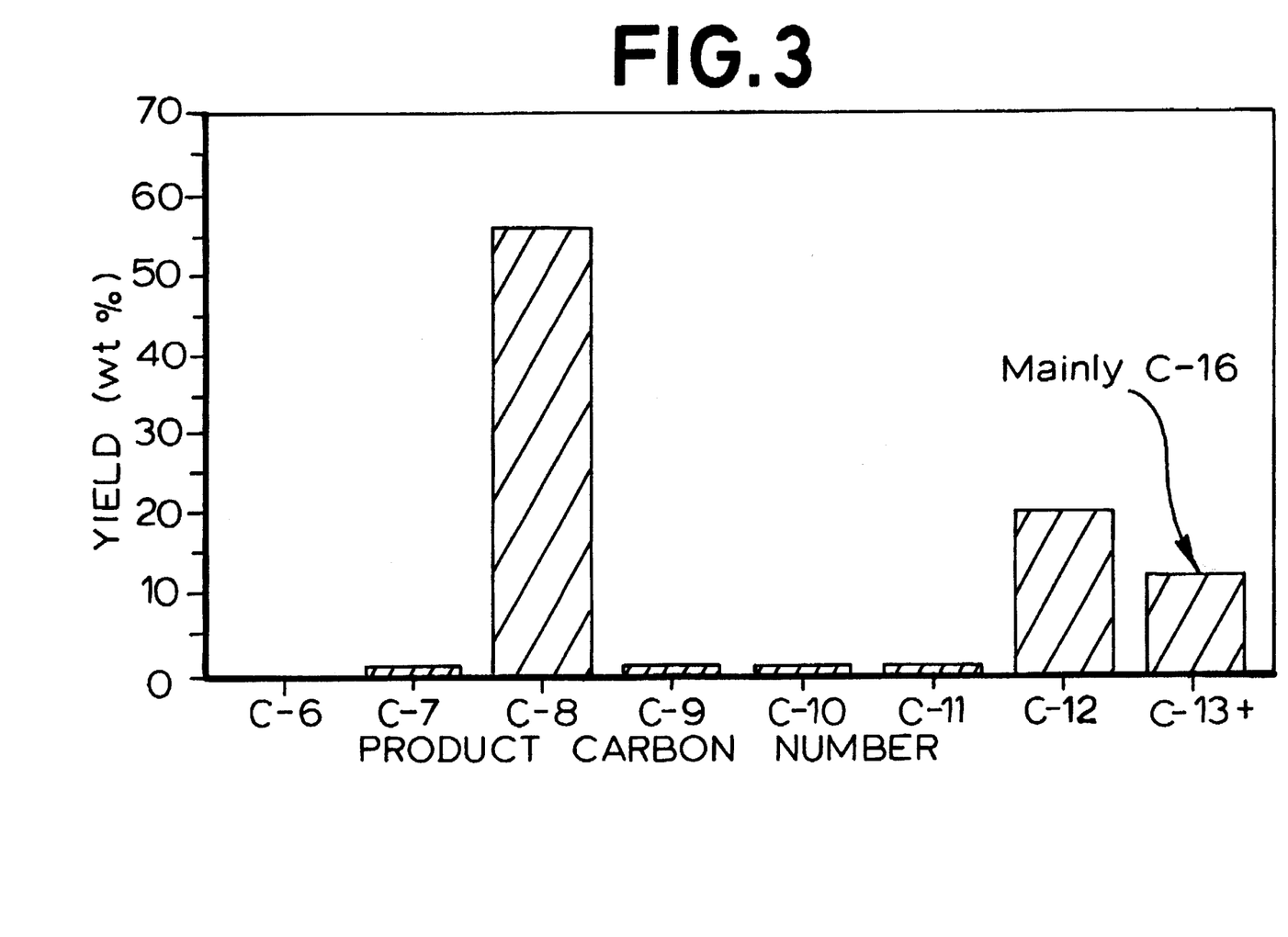
FIG. 3 is a graph showing carbon number distribution of the product of butene oligomerisation.
Figure 4:
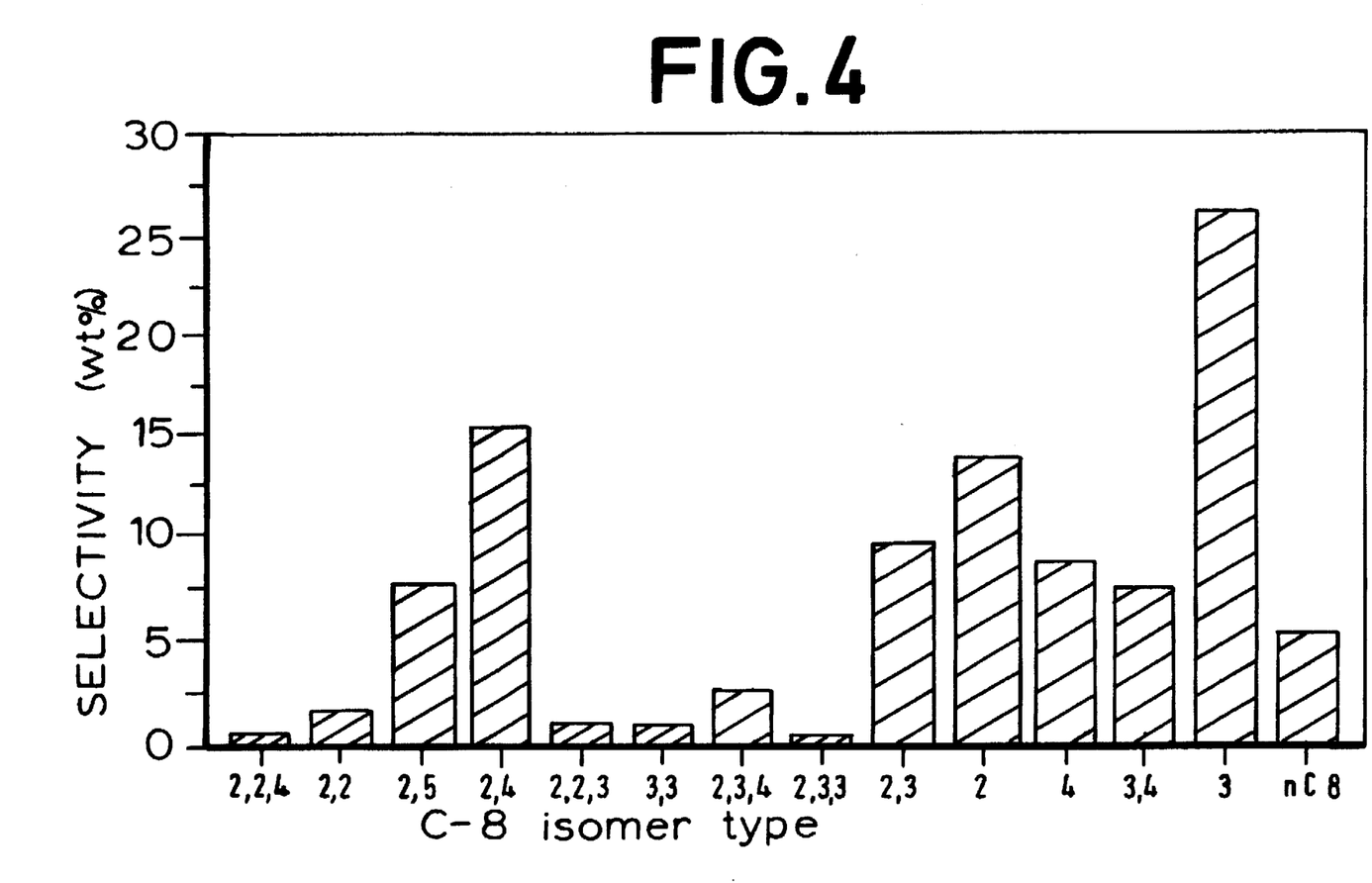
FIG. 4 is a graph showing the isomer distribution of C-8 product of butene oligomerisation.

A modified zeolite catalyst having the crystalline structure of ZSM-22 was prepared as described in Example 2(b). A feedstock containing, based on the total hydrocarbon content, approximately 64% n-butenes and 35% butane, the balance consisting essentially of propane and propene, was hydrated as described in Example 1 to give a water content of 0.18 molar %, based on the hydrocarbon content. The hydrated feedstock was passed through 8.5 g of the modified zeolite catalyst in a reactor at a pressure of 70 bar (7×10$^6$ Pa) at a temperature which was gradually raised between 205 and 255° C. The space velocity was from 1.75 to 2.40 weight/weight.hour. The reaction product was analysed. The carbon number distribution of higher hydrocarbons, calculated for the cumulative product over a one month period, is shown in FIG. 3. FIG. 4 shows the isomer distribution for C$_8$ product (excluding saturated products). The conversion was above 80%.

EXAMPLE 4

(a) Preparation of ZSM-22 Crystals 144.03 g Ludox AS40 (which contains 40% by weight SiO$_2$ in water, with ammonium ions as stabilising agent) was dissolved in 248.01 g water. In a separate vessel, 6.90 g Al$_2$(SO$_4$)$_3$·18H$_2$O were mixed with 351.18 g water and stirred until a clear solution was obtained, to which were added 15.49 g potassium hydroxide (87.5% purity). The solution was stirred, 33.45 g 1,6-diaminohexane were added, while continuing stirring, and the solution so obtained was added to the Ludox AS40 solution. Stirring was continued for five minutes. 787.1 g of the combined solution were placed in a stainless steel autoclave. The temperature was increased from room temperature to 160° C. at a rate of 1° C. per minute, and maintained at 160° C. for 48 hours while stirring at 100 rpm., during which time crystals were formed. The product was recovered from the mother liquor, washed with water until the pH fell to 9.7 and dried overnight at 120° C. The ZSM-22 precursor crystals so obtained were shown by X-ray diffraction to consist of ZSM-22, containing traces of ZSM-5 impurities. The precursor crystals, which had a SIO$_2$/Al$_2$O$_3$ ratio of 63, were of needle morphology, having an average needle length of 1 μm and a L/D ratio of between 4 and 7.

Longer needles were obtained by, for example, increasing the temperature of crystallisation or increasing the water content of the synthesis mixture.

(b) Effect of H-ZSM-22 Crystal Size on Catalyst Activity

Precursor crystals having an average needle length of 27 μm, at least 75 out of every hundred of the crystals having a needle length of from 20 to 34 μm were prepared as described in Example 4(a) above, calcined at 550° C. for 16 hours in oxygen, exchanged with NH$_4$Cl and calcined again at 550° C. for 16 hours to obtain the acidic form of ZSM-22 (H-ZSM-22).

A feedstock consisting, on a hydrocarbon basis, of 50.68% propene and 48.52% propane, the balance being made up of ethane and butane, was hydrated, using the hydration method described in Example 1, the water content being increased from 0.02 to 0.15 molar %, based on the hydrocarbon content of the feedstock. The hydrated feedstock was passed through the H-ZSM-22 crystals at a temperature of from 180° C., pressure of 70 bar (7×10$^6$ Pa) and space velocity of approximately 2 weight/weight hour. The conversion of propene to higher molecular weight hydrocarbons was monitored by GC. When the conversion had decreased to 80%, the temperature was increased such that the conversion remained above 80%. In this way, the % conversion was maintained at 80% or more until a maximum temperature of 235° C. was reached.

The catalyst life in weight product/weight catalyst was determined at the time at which the conversion became less than 80% at temperature 235° C. The catalyst life was determined in a similar manner for H-ZSM-22 crystals having average needle lengths of 27 μm, 15 μm, 7 μm and 1 μm, respectively. The catalyst lives of the crystals are given in Table 2.

In the case of the crystals having average length of 1 μm, the conversion remained at over 90% at temperature 225° C. after two months use and the reaction was then terminated.

TABLE 2

| Crystal Length μm* | Catalyst Life (weight product/weight catalyst) |
|---|---|
| 27 ± 7 | 252 |
| 15 ± 4 | 384 |
| 7 ± 2 | 636 |
| 1 ± 0.3 | 1240 |

*Based on SEM (scanning electron microscopy) analysis, at least 75 out of every hundred of the zeolite crystals were within the range given.

EXAMPLE 5

Effect of Temperature of Calcination of Zeolite Catalyst Precursor on Catalytic Activity of ZSM-22 and Other, Non-Needle-Shaped Zeolites (a)

Precursor crystals of ZSM-12 were obtained by preparing a synthesis gel containing 0.41M $Na_2O$, 0.89M tetraethyl ammonium oxide, 0.04M $Al_2O_3$, 10M $SiO_2$ and 80M water. After crystallisation in a static autoclave at 125° C. for 12 days, the solid material formed was recovered, washed, and dried. The crystals were divided into two batches. The first batch was exchanged with aqueous $NH_4Cl$ and heated in air to a temperature of 300° C. for 16 hours, and the second batch was heated in air to 550° C., for 16 hours, exchanged with aqueous $NH_4Cl$, and calcined again for a further 16 hours at 550° C. 9.9 g of the first batch of crystals were then placed in a reactor under a pressure of 70 bar ($7 \times 10^6$ Pa). A feedstock containing, based on the hydrocarbon content, 49.97% propene, 49.88% propane, the balance ethane and butane, and having a water content of 0.15 molar %, based on the hydrocarbon content of the feedstock, was passed over the catalyst at a space velocity of approximately 2 weight/weight.hour. The % propene conversion was monitored by GC at 180° C. and at 230° C. In each case less than 5% conversion was observed. In contrast, using 9 g of the second batch of crystals with a feedstock containing, based on hydrocarbons, 49.42% propene, 50.50% propane, the balance ethane and butane, and having a moisture content of 0.15 molar % based on the hydrocarbon content, initial conversion of over 95% was observed at 180° C. In the case of the second batch, no measurements were made at 230° C.

(b)

Precursor crystals of ZSM-22 and an average needle length of 27 μm were prepared as described in Example 4(a) and divided into two batches, the first batch being exchanged with aqueous HCl and calcined at 400° C. to give a modified zeolite catalyst having the crystalline structure of ZSM-22, and the second batch being calcined at 550° C., exchanged with $NH_4Cl$, and calcined again 550° C. Calcination was in each case carried out for 16 hours. 14.7 g of the first batch of crystals were placed in a reactor. A feedstock containing 49.20% propene, 47.95% propane, the balance ethane and butanes, based on hydrocarbon content, was fed to the reactor, after hydration in accordance with the hydration method described in Example 1 to give a water content of 0.15 molar %, based on the hydrocarbon content. The space velocity was from 1.45 to 2.05 weight/weight.hour. The pressure in the reactor was maintained at 70 bar ($7 \times 10^6$ Pa). The oligomerisation product was analysed. The procedure was then repeated using 15.4 g of the second batch of crystals, the feedstock containing, based on hydrocarbons, 48.70% propene, 48.42% propane, and having a water content of 0.15 molar % based on the hydrocarbon content of the feedstock, the balance ethane and butanes, and the space velocity being from 0.75 to 2.00 weight/weight.hour. The results are summarised in Table 3A for the first batch of crystals (modified zeolite catalyst) and in Table 3B for the second batch (H-ZSM-22). As shown in Tables 3A and 3B, the proportion of saturated $C_5$ to $C_{15}$ product is very small. The propene conversion decreases considerably more rapidly when H-ZSM-22 that has been calcined at 550° C. is used than when the modified zeolite catalyst is used.

The amount of aromatics formed was in each case less than 50 ppm.

TABLE 3A

| Space Vel. (weight/weight · hr) | 1.94 | 2.01 | 1.51 | 1.50 | 1.46 | 1.54 | 1.56 |
|---|---|---|---|---|---|---|---|
| Temperature (°C.) | 230 | 230 | 230 | 250 | 250 | 250 | 250 |
| No Days on Stream | 0.75 | 1.75 | 4.75 | 5.75 | 6.75 | 7.75 | 8.75 |
| Catalyst Life (weight prod/weight cat) | 17.1 | 40.9 | 91.1 | 106.7 | 121.2 | 135.0 | 148.5 |
| Catalyst Life (weight feed/weight cat) | 34.9 | 83.2 | 191.7 | 227.6 | 262.7 | 299.7 | 337.2 |
| Propene Conversion (%) | 99.78 | 99.90 | 94.10 | 88.36 | 83.66 | 76.28 | 72.72 |
| Selectivity (%) | | | | | | | |
| $C_5$ | 1.09 | 0.94 | 0.47 | 0.34 | 0.27 | 0.22 | 0.20 |
| $C_6$ | 17.26 | 26.64 | 56.62 | 65.96 | 70.01 | 75.85 | 77.60 |
| $C_7$ | 3.04 | 2.30 | 1.05 | 0.83 | 0.66 | 0.57 | 0.54 |
| $C_8$ | 2.89 | 2.16 | 0.69 | 0.52 | 0.41 | 0.34 | 0.33 |
| $C_9$ | 20.73 | 26.67 | 26.26 | 22.84 | 20.72 | 17.53 | 16.49 |
| $C_{10}$ | 5.18 | 3.73 | 1.05 | 0.73 | 0.63 | 0.47 | 0.48 |
| $C_{11}$ | 5.15 | 3.46 | 0.98 | 0.65 | 0.51 | 0.41 | 0.38 |
| $C_{12}$ | 18.23 | 18.95 | 10.00 | 7.22 | 6.03 | 4.31 | 3.80 |
| $C_{13}$ | 5.64 | 3.39 | 0.69 | 0.00 | 0.00 | 0.00 | 0.00 |
| $C_{14}$ | 5.06 | 2.58 | 0.49 | 0.00 | 0.00 | 0.00 | 0.00 |
| $C_{15}$ | 15.71 | 9.18 | 1.71 | 0.91 | 0.75 | 0.30 | 0.18 |
| $C_5$–$C_{15}$ Product from Cracking (%) (*) | 28.06 | 18.56 | 5.42 | 3.07 | 2.49 | 2.01 | 1.92 |
| Saturates in $C_5$–$C_{15}$ Product (%) | 6.1 | 5.0 | | | | | |

(*) SUM of $C_5 + C_7 + C_8 + C_{10} + C_{11} + C_{13} + C_{14}$

TABLE 3B

| Space Vel. (weight/weight · hr) | 1.98 | 1.99 | 1.64 | 1.13 | 0.78 | 0.88 | 0.81 |
|---|---|---|---|---|---|---|---|
| Temperature (°C.) | 230 | 230 | 230 | 250 | 250 | 250 | 250 |
| No Days on Stream | 0.75 | 1.75 | 4.75 | 5.75 | 6.75 | 7.75 | 8.75 |
| Catalyst Life (weight prod/weight cat) | 17.4 | 38.5 | 62.8 | 69.0 | 74.4 | 79.2 | 82.6 |

TABLE 3B-continued

| Catalyst Life (weight feed/weight cat) | 35.8 | 83.7 | 201.9 | 229.1 | 248.3 | 267.9 | 287.4 |
|---|---|---|---|---|---|---|---|
| Propene Conversion (%) | 99.81 | 90.60 | 42.08 | 46.84 | 57.77 | 51.10 | 35.36 |
| Selectivity (%) | | | | | | | |
| $C_5$ | 1.14 | 0.97 | 0.29 | 0.26 | 0.25 | 0.30 | 0.22 |
| $C_6$ | 20.69 | 44.93 | 78.62 | 72.51 | 69.54 | 68.47 | 75.89 |
| $C_7$ | 3.21 | 1.80 | 0.69 | 0.83 | 0.75 | 0.76 | 0.64 |
| $C_8$ | 2.87 | 1.57 | 0.41 | 0.49 | 0.47 | 0.52 | 0.39 |
| $C_9$ | 24.53 | 29.57 | 15.46 | 19.65 | 21.83 | 21.84 | 17.99 |
| $C_{10}$ | 4.55 | 2.05 | 0.52 | 0.66 | 0.69 | 0.74 | 0.58 |
| $C_{11}$ | 4.35 | 2.09 | 0.43 | 0.58 | 0.56 | 0.63 | 0.45 |
| $C_{12}$ | 17.76 | 12.07 | 3.37 | 4.58 | 5.37 | 5.43 | 3.80 |
| $C_{13}$ | 4.49 | 1.49 | 0.00 | 0.00 | 0.00 | 0.45 | 0.00 |
| $C_{14}$ | 3.74 | 1.12 | 0.00 | 0.00 | 0.03 | 0.26 | 0.00 |
| $C_{15}$ | 12.66 | 2.34 | 0.19 | 0.43 | 0.49 | 0.61 | 0.04 |
| $C_5-C_{15}$ Product from Cracking (%) (*) | 24.36 | 11.09 | 2.35 | 2.82 | 2.77 | 3.65 | 2.29 |
| Saturates in $C_5-C_{15}$ Product (%) | 6.8 | 4.2 | | | | | |

(*) SUM of $C_5 + C_7 + C_8 + C_{10} + C_{11} + C_{13} + C_{14}$

EXAMPLE 6

Comparison of Activities and Rates of Deactivation of H-ZSM-22 and H-ZSM-5 in Olefin Oligomerisation (a)

A feedstock consisting of, based on the hydrocarbon content, 48.48% propene, 48.37% propane, the balance consisting of ethane and butane, and having a water content of not more than 0.02 molar %, based on the hydrocarbon content, was passed through 9.7 g H-ZSM-5 crystals $SiO_2$/ $Al_2O$ ratio 65) in a reactor at a flow rate of approximately 40 ml/hour. The temperature in the reactor was maintained at 230° C. and the pressure at 70 bar ($7 \times 10^6$ Pa). The content of the product was monitored using GC.

(b)

The process of (a) was repeated except that the feedstock contained 49.12% propene and 47.95% propane and the zeolite H-ZSM-5 was replaced by 7.8 g H-ZSM-22 ($SiO_2$/ $Al_2O_3$ ratio 65). In contrast to the H-ZSM-5 crystals used in (a), the H-ZSM-22 crystals are of needle-shaped configuration having a length to diameter ratio of greater than 3 and an average length of less than 30μ.

As illustrated by the measurements given in Table 4, H-ZSM-5 is less active than H-ZSM-22 and becomes deactivated more quickly. Thus, at a catalyst life (weight feed/ weight catalyst) of 93.4, the conversion of propene to higher molecular weight hydrocarbons had fallen to 17.75% for H-ZSM-5. For H-ZSM-22, at a catalyst life (weight feed/ weight catalyst) of 98.6 the conversion is 94.91 and at a catalyst life of 247.5 the conversion had fallen only to 53.11%.

The amount of aromatics produced in the process of (b) was less than 50 ppm.

TABLE 4

| Catalyst | ZSM-5 | ZSM-5 | ZSM-5 | ZSM-22 | ZSM-22 | ZSM-22 |
|---|---|---|---|---|---|---|
| Space Vel. (weight/weight · hr) | 2.23 | 2.15 | 1.99 | 1.44 | 1.40 | 1.60 |
| No Days on Stream | 0.25 | 0.88 | 1.88 | 2.83 | 3.83 | 6.83 |
| Catalyst Life (weight prod/weight cat) | 4.3 | 8.1 | 12.2 | 29.2 | 42.3 | 72.4 |
| Catalyst Life (weight feed/weight cat) | 13.4 | 45.7 | 93.4 | 98.6 | 132.2 | 247.5 |
| Propene Conversion (%) | 65.42 | 24.45 | 17.75 | 94.91 | 79.97 | 53.11 |
| Selectivity (%) | | | | | | |
| $C_5$ | 0.65 | 0.71 | 0.71 | 0.64 | 0.48 | 0.38 |
| $C_6$ | 5.09 | 18.67 | 31.70 | 22.87 | 41.78 | 57.17 |
| $C_7$ | 2.70 | 2.17 | 1.75 | 2.32 | 1.50 | 0.98 |
| $C_8$ | 3.48 | 2.16 | 1.53 | 1.74 | 1.05 | 0.68 |
| $C_9$ | 37.88 | 45.52 | 42.23 | 32.33 | 31.37 | 28.05 |
| $C_{10}$ | 4.62 | 2.60 | 1.93 | 2.64 | 1.55 | 0.86 |
| $C_{11}$ | 4.71 | 2.35 | 1.65 | 2.39 | 1.27 | 0.60 |
| $C_{12}$ | 21.78 | 13.83 | 10.40 | 16.39 | 11.53 | 7.35 |
| $C_{13}$ | 5.08 | 2.77 | 1.99 | 3.66 | 1.94 | 0.00 |
| $C_{14}$ | 3.66 | 1.97 | 1.53 | 2.11 | 0.00 | 0.00 |
| $C_{15}^+$ | 10.36 | 7.25 | 4.58 | 12.94 | 7.51 | 3.92 |
| $C_5-C_{15}$ Product from Cracking (%) (*) | 24.89 | 14.73 | 11.09 | 15.47 | 7.81 | 3.51 |
| Saturates in $C_5-C_{15}$ Product (%) | | | | 4.8 | 3.2 | 2.4 |

(*) SUM of $C_5 + C_7 + C_8 + C_{10} + C_{11} + C_{13} + C_{14}$

We claim:

1. A process for oligomerising $C_2-C_{12}$-alkenes to produce olefins of initial boiling point in the range 30° to 310° C., comprising contacting a $C_2-C_{12}$-alkene-containing feedstock having a water content of from 0.05 to 0.25 molar %, based on the hydrocarbon content of the feedstock, with a zeolite structure catalyst selected from the group consisting of TON, MTT, MFI, MEL, MTW, EUO, H-ZSM-57, ferrierites, offretites, H-ZSM-4, H-ZSM-18, Zeolite Beta, faujasites, zeolite L, mordenites, erionites and chabazites.

2. A process as claimed in claim 1, wherein the catalyst has crystals of needle morphology with a length:diameter ratio of not less than 3.

3. A process claims in claim 1 or claim 2, wherein the zeolite structure catalyst is a TON, H-ZSM-22 catalyst having the crystalline structure of ZSM-22.

4. A process as claimed in claim 1, wherein the catalyst has been calcined at a temperature of from 120° C. to 430° C. for a period of from 5 days to 5 hours.

5. A process as claimed in claim 1, wherein contacting is carded out at a temperature not exceeding 260° C.

6. A process as claimed in claim 3, in which the crystals have a length not exceeding 30 μm.

7. A process as claimed in claim 1, in which the feedstock contains $C_3$–$C_6$-alkenes.

8. A process as claimed in claim 1, wherein the catalyst comprises crystals having the porous aluminosilicate structure of ZSM-22 which have been formed using an organic promoter, and which contain residual promoter or a decomposition product thereof.

* * * * *